United States Patent [19]

Weeks

[11] Plant 4,323

[45] Oct. 24, 1978

[54] ROSE PLANT

[76] Inventor: O. L. Weeks, 926 W. Philadelphia St., Ontario, Calif. 91761

[21] Appl. No.: 837,745

[22] Filed: Sep. 29, 1977

[51] Int. Cl.[2] ..... A01H 5/00
[52] U.S. Cl. ..... Plt./2
[58] Field of Search ..... Plt./2, 5, 26

*Primary Examiner*—Robert E. Bagwill
*Attorney, Agent, or Firm*—Frank B. Robb

[57] ABSTRACT

There is disclosed a new variety of climber rose which is completely distinctive from its parent "China Doll" U.S. Plant Pat. No. 678, in that it grows as a climber, the parent being a low bush, and the flowers are produced on stems that grow as laterals in contrast to the clusters which characterize the parent, the color of the flowers and leaves being otherwise substantially identical as can be determined.

1 Drawing Figure

The present invention relates to a new and distinct variety of rose plant of the climber class which was discovered by me as a sport of plants of the variety known as "China Doll" U.S. Plant Pat. No. 678, whose parentage and derivation is adequately described in that patent.

The plant upon which this Sport was discovered was found in a routine inspection of a large number of bush "China Doll" plants which are grown continuously by me, and I noticed that one plant had produced a distinctly climbing cane.

Steps were taken immediately by me to preserve this Sport and to asexually produce the same, this having been effected by budding in regular growing fields in Wasco, Calif.

Observations of the asexual reproductions which were continued as the plant was grown, conclusively established that the new Sport was substantially identical with the parent variety "China Doll" as far as the flowers and leaves and other characteristics were concerned but distinct therefrom and outstandingly noticeable because of its climbing habit and by reason of the fact that the flowers are produced on stems that grow as laterals from the climbing canes.

The various distinguishing features and characteristics of the new plant are fixed and transmissible by asexual reproduction, maintaining the same in continued growth, with the large distinction remaining of the climbing habit, which so far as the plant "China Doll" is known in my experience has never previously exhibited any climbing habit and I am therefore persuaded that this Sport is definitely new and distinct.

While the climbing habit and manner of growth of the flowers are the primary distinguishing characteristics from the parent variety the climbing habit is clearly established by the fact that long strong canes which obtain an average mature height of 4–6 feet are produced and while this is the major distinguishing characteristic, the flowers as before stated are virtually the same as those of "China Doll" U.S. Plant Pat. No. 678.

It may suffice to summarize the following unique combination of characteristics which are outstanding by stating that the same are:

1. The long extremely strong and vigorous canes which attain an average height of 4 and 6 feet;

2. The habit of bearing its flowers on stems which grow as laterals from the climbing canes:

3. The retention of the attractive flowers and foliage of the parent variety "China Doll."

As before stated asexual reproduction of my new variety by budding at Wasco, Calif. shows that the aforementioned characteristics and distinctions come true to form and are established and transmitted through succeeding generations.

In the accompanying drawing, a typical specimen of the vegetative growth of my new variety is disclosed, as compared with a typical low growing bush of the parent variety "China Doll," which it will be noted that the long canes and laterals are as before described, and provide the necessary distinguishing characteristics in and of themselves.

While no detailed description of my new variety is felt necessary as to the other characteristics particularly with reference to the color of the flowers and foliage, the minimum aspects are setforth, and only those which are clearly distinctive described in detail.

Type: Hardy; climber; outdoor; seedling.
Class: Climber.
Breeding: Discovered as a sport on the variety known as "China Doll" U.S. Plant Pat. No. 678.
Propagation: Holds its distinguishing characteristics through successive propagation by budding.

FLOWERS

Locality where grown and observed: Wasco, Calif.
Flowers borne: Several to a stem on laterals grow from the climbing canes.
Quantity of bloom: Typical polyantha.
Fragrance: Slight, tea to spicey.
Growth:
- *Habit.*—Tall 4–6 feet, much branched.
- *Growth.*—Vigorous.
- *Canes.*—Long, strong vigorous canes, attaining an average mature height of 4 to 6 feet.
- *Main stems.*—Large prickles — few short hooked downward with the long narrow base. Small prickles — None. Hairs — None.

Flowers on stems grow as laterals from the climbing canes.

I claim:

1. A new and distinct variety of rose plant of the climbing class, substantially as herein shown and described, characterized particularly as to novelty by the long, strong and vigorous canes which attain an average mature height of 4 to 6 feet, the habit of bearing flowers on stems which grow as laterals from the climbing canes while retaining the desirable characteristics of polyanthas in color and quantity of blooms and foliage.

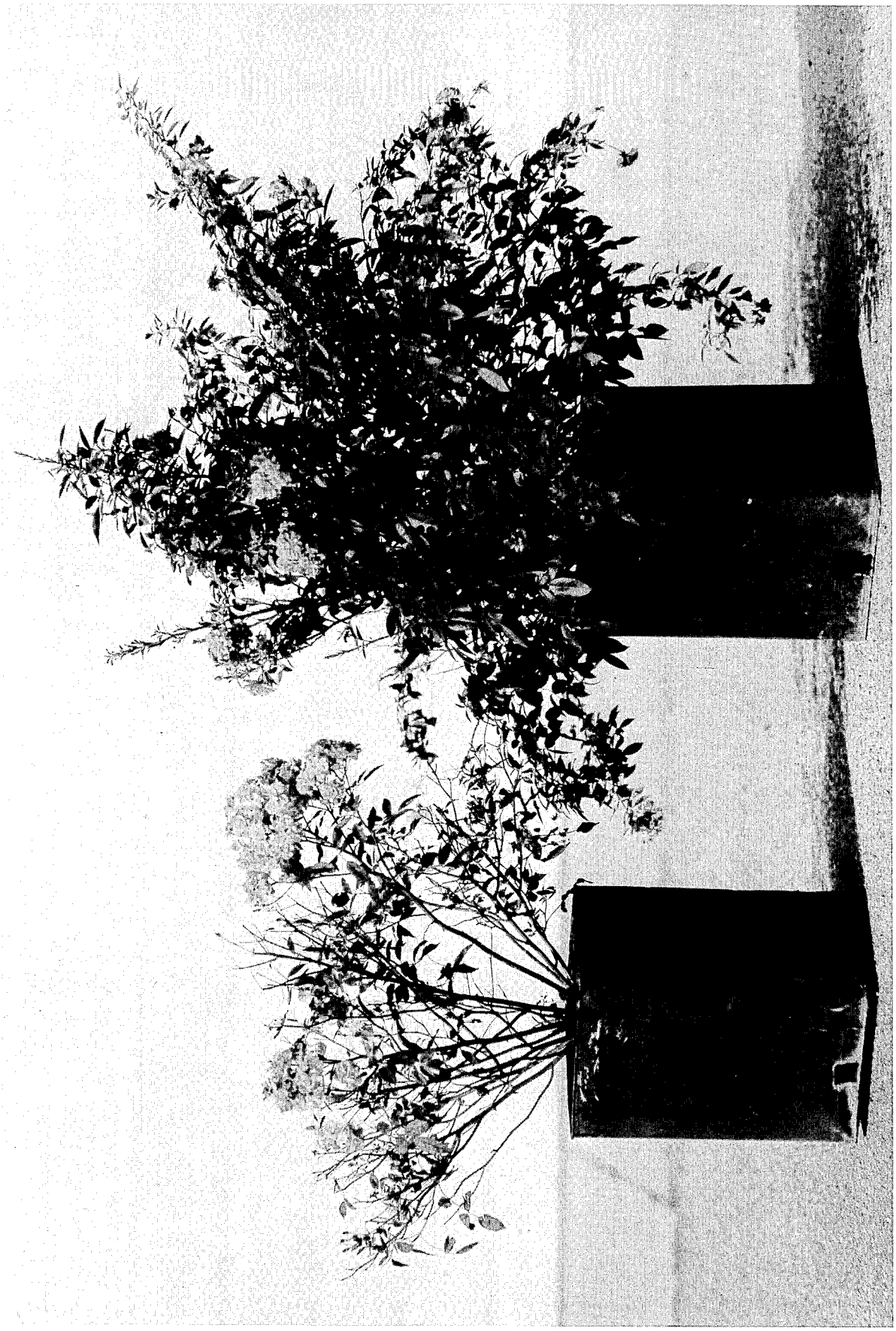

* * * * *